United States Patent
Marigza

[11] Patent Number: 5,266,031
[45] Date of Patent: Nov. 30, 1993

[54] METHOD AND DEVICE FOR DETERMINING TENTATIVE MAXILLO-MANDIBULAR CENTRIC OCCLUSION

[76] Inventor: Rupert M. Marigza, 1901 Wildwood Ave., Nashville, Tenn. 37212

[21] Appl. No.: 946,181

[22] Filed: Sep. 16, 1992

[51] Int. Cl.5 .................................. A61C 9/00
[52] U.S. Cl. ........................ 433/71; 433/214
[58] Field of Search ............ 433/37, 48, 68, 71, 433/214

[56] References Cited

U.S. PATENT DOCUMENTS

| | | | |
|---|---|---|---|
| 1,728,199 | 9/1929 | Eberhart | 433/214 |
| 2,183,624 | 12/1939 | Schwartz | 433/71 |
| 2,594,830 | 4/1952 | Wade | 433/71 |
| 3,217,067 | 11/1965 | Tencate | 264/18 |
| 3,228,107 | 1/1966 | Zandberg | 433/71 |
| 3,663,141 | 5/1972 | Alain et al. | 425/175 |
| 3,813,777 | 6/1974 | Van Handel | 32/2 |
| 4,115,488 | 9/1978 | Colpitts | 264/17 |
| 4,307,044 | 12/1981 | Perez | 264/19 |
| 4,324,547 | 4/1982 | Arcan et al. | 433/71 |
| 4,517,043 | 6/1985 | Martin | 156/196 |
| 4,624,640 | 11/1986 | Tesini | 433/71 |
| 4,657,509 | 4/1987 | Morris | 433/37 |
| 4,745,961 | 5/1988 | Salandra | 164/14 |
| 4,846,682 | 7/1989 | Ootsubo | 433/167 |
| 4,983,331 | 1/1991 | Wise | 264/16 |
| 5,011,407 | 4/1991 | Pelerin | 433/48 |
| 5,059,120 | 10/1991 | Lee | 433/37 |

FOREIGN PATENT DOCUMENTS 2630905  11/1989  France ......................... 433/214

Primary Examiner—Gene Mancene
Assistant Examiner—Nicholas D. Lucchesi
Attorney, Agent, or Firm—Mark J. Patterson; Edward D. Lanquist, Jr.; I. C. Waddey, Jr.

[57] ABSTRACT

The present invention relates to a device for determining tentative centric occlusion of an upper and a lower of a patient. The device generally has a bite block which surrounds a handle. The bite block has an inner layer of hard wax surrounded by an upper and lower layers of soft wax. Tracks can be put in the exposed surfaces of the soft wax to generally conform to the patient's upper and lower existing teeth or gums. Recessed areas can be placed in the hard wax to generally receive the existing teeth of the patient. When recessed areas are used, ridges exist in the soft wax to fill the recessed areas. The soft wax is intended to allow proper impression of the exposed gingiva whereas the hard wax is necessary for obtaining the impression of the existing teeth.

15 Claims, 3 Drawing Sheets

METHOD AND DEVICE FOR DETERMINING TENTATIVE MAXILLO-MANDIBULAR CENTRIC OCCLUSION

BACKGROUND OF THE INVENTION

The present invention relates generally to a device for determining the required size and shapes of dentures or partials and more particularly to a device for determining tentative centric occlusion and registration of the upper and a lower bite of a dental patient.

The type of food we eat, how fast and for how long depends on the neuromusculature. Therefore, neuromusculature is the governor of mandibular function. During the dentulous state of an individual the masticatory apparatus functions in centric occlusion (C.O.). When the teeth are gone, we do not know how to find the centric occlusion, except that we know that the muscles function most efficiently when in centric occlusion. Therefore, until now, centric relation has been used when dentition is lost in the effort to find the centric occlusion. It has also been suggested by well known authors that the point of centric occlusion is located one or two millimeters in front of the point of centric relation. Somewhere anterior to centric relation is the point of function as determined by the neuromusculature. When we find that position, we set our teeth to it. It is at that position that the patient is functioning at functional occlusion and masticates his food most efficiently.

When one attempts to lift a chair, it is much easier to lift the chair closer to the body because the muscles of the trunk and arms function better when the load is nearer the fulcrum and the muscles always brace themselves toward the center of the body or fulcrum. The mandible is likewise efficient. Toward the posterior, in the area of the second molar, the mandible functions maximally. When the mandible is braced to the glenoid fossa by the vectors and directions of the muscle fibers, the mandible in this state is in functional occlusion. However, if we attempt to push or position the mandible with finger pressure, we introduce a non-functional stimulus and, therefore, we might be in centric relation or other positions but not the functional occlusal position because the soft tissue around the bony condyle is artificially compressed.

It will be appreciated by those skilled in the art that in order to fit dentures, one must record a tentative horizontal maxilla-mandibular relationship in the partially and fully edentulous mouth. Further, the face-bow registration of the patient must also be recorded, as well as the vertical dimension of occlusion. Unfortunately, in the past, obtaining these measurements has been time consuming, typically taking one of the four or more separate visits to the dentist in order to deliver a completed, properly fitting denture. One of the primary reasons for this in the prior art is the inability of prior art devices to register adequate soft tissue (gingival) likeness while preventing distortions by the use of a harder wax bite. It is known that materials in contact with tissue be bi-laterally uniform in firmness, inert, and non-abrasive, all at ambient physiological temperatures.

One prior art method and device is disclosed in U.S. Pat. No. 4,657,509 issued to P. Morris on Apr. 14, 1987. The Morris patent discloses an impression tray which is malleable at temperatures of 150° Fahrenheit yet rigid at body temperature. Unfortunately, this device has one consistent layer of material and does not distinguish the need between obtaining impression of the existing teeth versus the impression of the exposed gingiva.

Another such device is disclosed in U.S. Pat. No. 3,217,067 issued to R. Tencate on Nov. 9, 1965. Like Morris, Tencate fails to recognize the difference in texture between existing teeth and exposed gingiva.

U.S. Pat. No. 3,663,141 issued to A. Clenet, et al. on Feb. 26, 1970 discloses an impression device in which two halves of an impression are made separately. One-half of the impression is made of the exposed buccal tissue whereas the other half is made of the existing teeth. Unfortunately, this device requires four different molds, two for the upper and two for the lower.

U.S. Pat. No. 4,115,488 issued to R. Colpitts on Sep. 19, 1978, discloses a single layer impression. Unfortunately, like much of the prior art, Colpitts fails to recognize the difference in texture of the exposed gingiva from the existing teeth.

U.S. Pat. No. 4,307,044 issued R. Perez on Dec. 22, 1981, also discloses a single layer impression which fails to recognize the difference in texture of the exposed gingiva from the existing teeth.

U.S. Pat. No. 4,517,043 issued to R. Martin, et al on May 14, 1985, discloses a single layered impression which fails to recognize the difference in texture of the exposed gingiva from the existing teeth.

U.S. Pat. No. 4,846,682 issued to Ootsubo on Jul. 11, 1989, discloses a single layered impression which fails to recognize the difference in texture of the exposed gingiva from the existing teeth.

U.S. Pat. No. 4,983,331 issued to T. Wise on Jan. 8, 1991, discloses the use of a single layered impression which fails to recognize the difference in texture of the exposed gingiva from the existing teeth.

U.S. Pat. No. 5,059,120 issued to R. Lee on Oct. 22, 1991, discloses a handle having impression pads which are of the same consistency throughout.

U.S. Pat. No. 4,745,961 issued to A. Salandra on May 24, 1988, discloses a single layered impression. Although the Salandra patent discloses the use of beeswax, it is merely used as a coating for a set-up and is not used for multi-layered impressions.

U.S. Pat. No. 3,813,777 issued to A. Van Handel, et al on Jun. 4, 1974 discloses a single layered impression. Although the Van Handel patent discloses a layer of wax over a layer of plastic, the plastic is not impressed.

What is needed, then, is a device which recognizes the difference in exposed gingiva tissue as compared to existing teeth. This needed device must record the tentative horizontal maxilla-mandibular relationship or centric occlusion in the partially or fully edentulous mouth. This needed device must help record the arbitrary face-bow registration. This device must establish and record the tentative vertical dimension of occlusion. This device must eliminate at least one of the chair-side appointments of health compromised patients. This device must be used in connection with a three, as opposed to a four, appointment denture technique. This device is presently lacking in the prior art.

SUMMARY OF THE INVENTION

The present invention relates to a device for determining tentative centric occlusion for an upper and a lower denture of a patient. The device generally has a bite block which surrounds a handle. The bite block has an inner layer of hard wax surrounded by outer layers of soft wax. Tracks can be put in the exposed surfaces of the soft wax to generally conform to the patient's upper and lower existing teeth or gums. Recessed areas can be placed in the hard wax to generally receive the existing teeth of the patient. When valleys are used, ridges exists in the soft wax to fill the valleys. The soft wax is intended to allow proper impression of the exposed gingiva whereas the hard wax is necessary for obtaining the impression of the existing teeth.

The device is made thicker by use of a thicker layer of hard wax towards the back of the device so as to stimulate the patient's muscles to position the lower jaw in centric occlusion to the upper jaw.

Accordingly, one object of the present invention is to provide a device to record the tentative horizontal maxilla-mandibular relationship in the partially or fully edentulous mouth.

Still another object of the present invention is to help record the arbitrary face-bow registration.

Still another object of the present invention is to establish and record a tentative vertical dimension of occlusion.

A still further object of the present invention is to eliminate at least one chair side appointments of health-compromised patients.

Still a further object of the present invention is to provide a device which can eliminate one appointment in denture fitting.

Still another object of the present invention is to provide a device which takes into account the softness of texture of the gingiva as compared to the hardness of the existing teeth.

Another object of the present invention is to provide a means for stimulating the muscles of the patient toward proper positioning of the upper and lower jaw prior to bite registration.

DESCRIPTION OF THE PREFERRED EMBODIMENT

Figure 1:
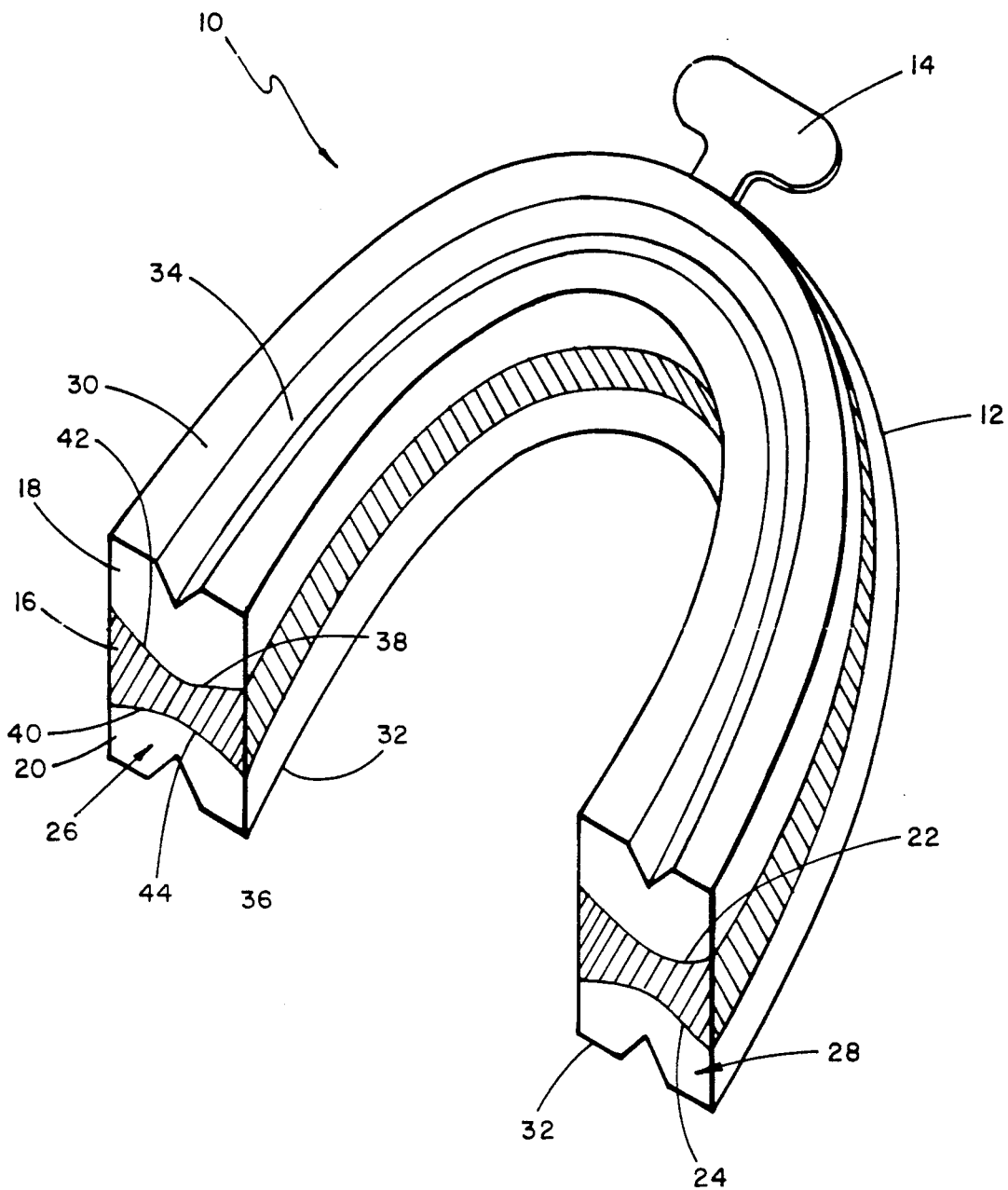
FIG. 1 is a perspective view of the device of the present invention.

Referring now to FIG. 1 there is shown generally at 10 the device for determining tentative centric relation of an upper and lower of a patient. Device 10 has a generally u-shaped bite block 12 and handle 14. Bite block 12 has layer of hard wax 16 surrounded by first layer of soft wax 18 and second layer of soft wax 20. Layer of hard wax 16 has upper surface 22 and lower surface 24. Bite block 12 has first end 26 and second end 28. In FIG. 1, first end 26 is partially cut away to show layering. However, ends 26, 28 of bite block 12 can be cut to show the layering or can be covered with a layer of soft wax completely surrounding the entire layer of hard wax 16. Device 10 has upper face 30 and lower face 32. Upper face 30 has first guide track 34 whereas lower face 32 has second guide track 36. First soft layer 18 has first ridge 38 whereas second soft layer 20 has second ridge 40. Ridges 38, 40 conform respectively to first recessed area 42 and second recessed area 44 in layer of hard wax 16. In the preferred embodiment, handle 14 is positioned between first end 26 and second end 28. Layers of wax 16, 18, 20 are sufficiently malleable if heated such that first end 26 can be moved with respect to second end 28 to obtain substantial alignment with patient's bite.

Figure 2:
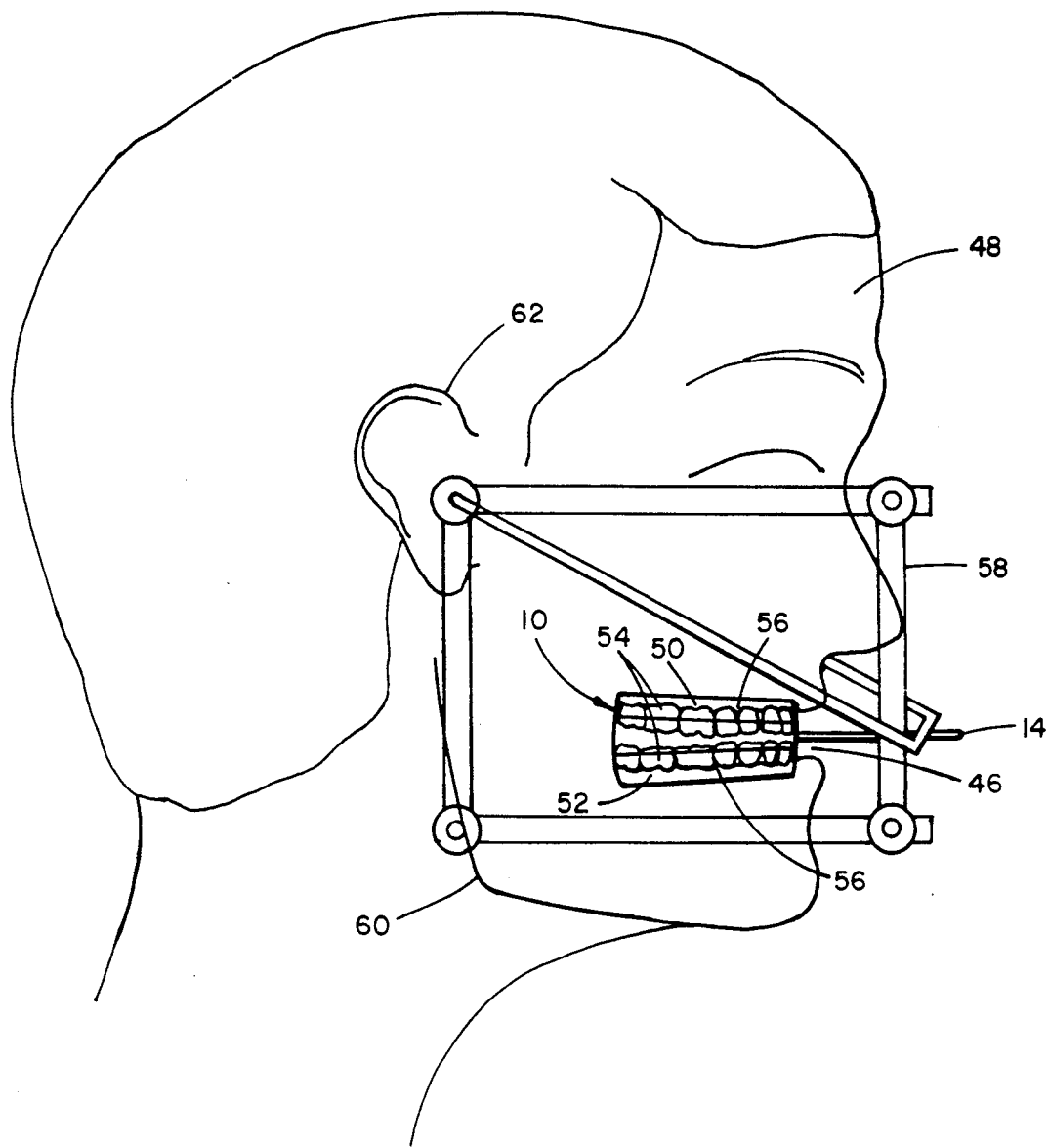
FIG. 2 is a side view of the device in a patient's mouth.

Referring now to FIG. 2 there is shown generally at 10 the device of the present invention as used in mouth 46 of patient 48. Patient 48 has upper dental tissue 50 and lower 52, each having teeth 54 and gingiva 56. In this particular embodiment, handle 14 is received by brace 58 which is generally aligned with patient's jaw 60 and ear 62. However, any type of brace can be used to limit movement of device 10 during the hardening of wax.

Figure 3:
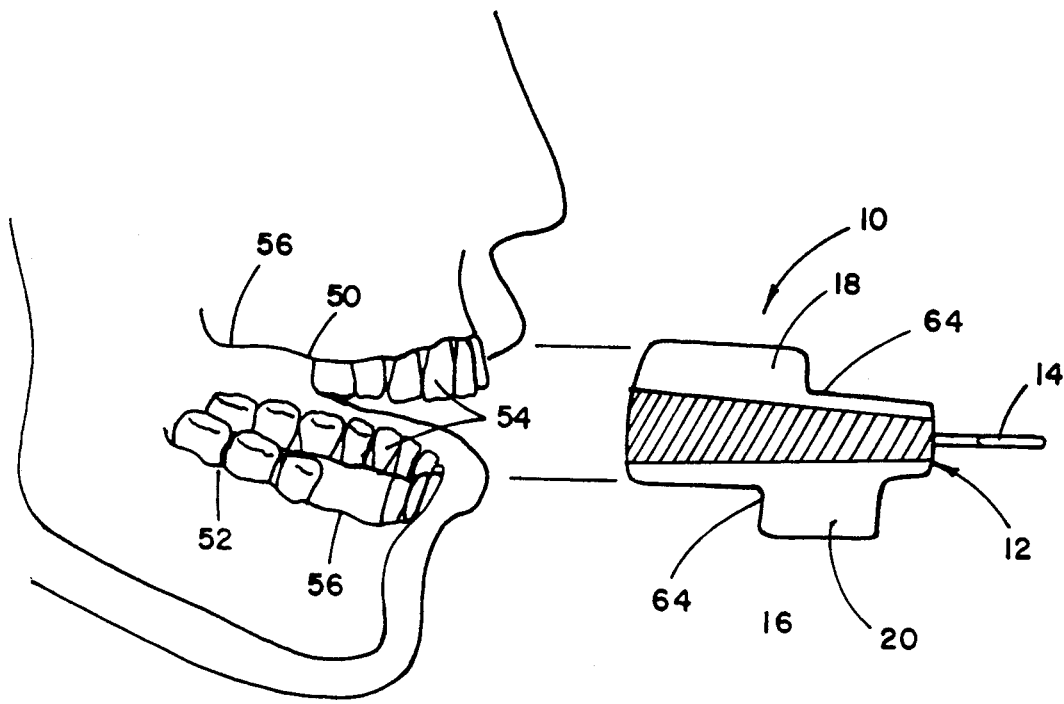
FIG. 3 is an exploded side view of one embodiment of the present invention positioned outside a patient's mouth.

Referring now to FIG. 3 there is shown generally at 10 still another embodiment of the device of the present invention. In this instance, upper 50 and lower 52 of patient 48 are partially edentulous, with the remaining natural teeth designated by 54. Portions of first layer of soft wax 18 and second layer of soft wax 20 are removed where there are existing teeth 54. This prevents an excess amount of soft wax from building up around existing teeth 54. Existing teeth 54 are impressed into layer of hard wax 16 because the key measurements of the remaining teeth are the alignment and the height but not the shape. As a result, cut outs 64 are made in layers of soft wax 18, 20. Soft wax 18, 20 remains where teeth 54 do not exist in gingiva 56.

Figure 4:
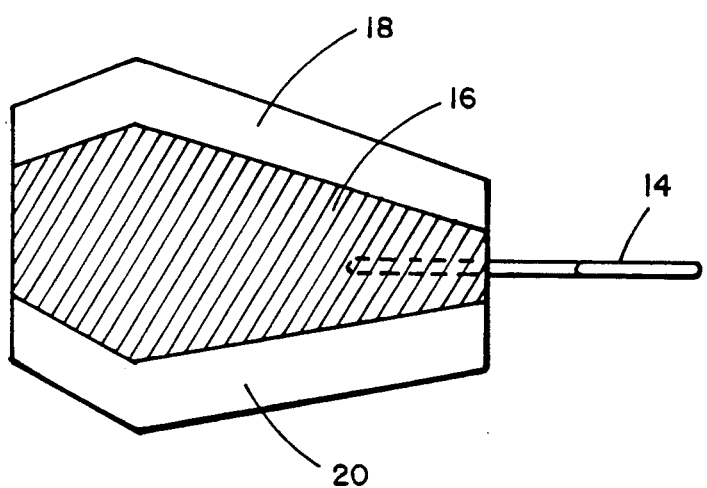
FIG. 4 is a side view of the device of the present invention.

In FIG. 4, the shaping of the device at the rear or open end of the device can be seen, with the thickness of the hard wax layer 16 increased in proportion to the thickness of soft wax layers 18 and 20. By using this shape, the muscles of the patient are stimulated to position the upper and lower jaw in centric occlusion.

In the preferred embodiment, device 10 is first soaked in a bowl of clean, warm water at substantially 35°-40° C. The distance between first end 26 and second end 28 is measured with orientation of the patient's mandible to the maxilla. The device is then returned to the water bath for another minute or two until the desired softness is obtained. Device 10 is then positioned in the desired shape in relation to patient's mouth and the patient is asked to bite into the device while the dentist monitors the predetermined vertical dimensions at a mid-line reference mark for the device. This device can then be returned to the water bath to adjust the horizontal thickness to get the desired height of the wax to increase or decrease the vertical dimensions. In the preferred embodiment, the patient is asked to bite with the back teeth first prior to this bath and then asked to bite with the front teeth after the bath. After the bite, the device is chilled. After chilling, the device is returned to the mouth for final inspection. Soft wax layers 18, 20 are laterally squeezed to build up the soft wax to gain tissue detail and maximum coverage for stability and accuracy. This wax can be molded to increase or decrease the height to obtain the desired vertical dimensions. Teeth 54 penetrate soft wax 18, 20 very easily and are impressed into hard wax 16. Where teeth 54 do not exist, an impression of gingiva 56 is gained into soft wax 18, 20 which would not have otherwise been gained into insufficient detail into hard wax 16.

The cross section of device 10, in the preferred embodiment, is substantially rectangular except for guide track 34, 36.

Device 10 is substantially U-shaped or horseshoe shaped to assimilate the bulk and curvature of the orthodonture of the patient.

In the preferred embodiment, the device of the present invention enables a three appointment denture fitting. During the first appointment, a close fitting tray is selected. An alginate or snap impression is made. When the appropriate size is determined, the device is soaked in warm water at substantially 35°–40° Celsius until soft and moldable which usually takes five to eight minutes. The device is then molded to grossly fill up existing interocclusal space. The mandible is guided in centric occlusion, assuming for purposes of this embodiment that the points of centric occlusion and centric relation are identically located. This can be done by instructing the patient to curl his or her tongue to the roof of the mouth while the dentist or technician applying the device guides the mandible in the most retruded, relaxed state of muscles. The device is chilled and placed into a zip lock bag with cold water. An impression is poured into the device and the device is sent to the lab.

During the second appointment, with a stabilized base plate and teeth set up in place on the maxillary and mandibular ridges, two layers of softened beeswax wafers are softened. The trial base is stabilized with common adhesive powder. The final centric registration is taken using the same method as described above. The teeth are reset to the desired aesthetic location. The vertical dimensions can be altered or corrected if necessary before taking the final centric registration. The interocclusal wax is chilled with a water syringe and set aside. The upper and lower trial set up is molded after border molding and refitting. The technician then mixes the final wash impression providing enough setting time to obtain two final impressions. The base plate with the wash impression material is placed with the maxillary first and the mandibular with bite registration wash in place. The teeth are guided into preregistered concentric relation into the wax registration device. The patient is instructed to maintain gentle but firm pressure for the next two minutes with lips together. The registration device is removed, washed, and disinfected.

During the third appointment, the dentures are inserted after necessary adjustment.

The size of device 10 and layers 16, 18, 20 is determined by orthodonture of patient 48.

The hard wax layer 16 of device 10 can be made of any approved dental wax, such as those meeting American Dental Specification 24. A hard wax made of 75% paraffin or ceresin, plus conventional and well known resins and natural waxes will work. Soft wax layers 18 and 20 in the preferred embodiment will be made of conventional hygienic beeswax.

Thus, although there have been described particular embodiments of the present invention of a new and useful device for determining tentative centric relation of a patient's upper and lower, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A device for taking an impression of an upper and a lower bite of a dental patient comprising:
   a. a layer of hard wax shaped for insertion into the mouth of said patient, said layer of hard wax having an upper surface and a lower surface;
   b. a first layer of soft wax attached to said layer of hard wax promixate said upper surface;
   c. a second layer of soft wax attached to said layer of hard wax proximate said lower surface;
   d. said device being U-shaped and having a closed segment and an open segment; and
   e. said layer of hard wax increases proportionally in thickness from said closed segment toward said open segment thereby adapting said device to stimulate said patient's upper and lower jaws into a position of centric occlusion.

2. The device of claim 1 wherein said soft wax comprises beeswax.

3. The device of claim 1 wherein said device comprises first and second ends defining a substantially horse-shoe shape, and a handle attached to said device between said first end and said second end.

4. The device of claim 3 wherein said first end can be manipulated at room temperatures in relation to said second end.

5. The device of claim 1 wherein:
   a. said device has an upper face and a lower face;
   b. said upper face has a first guide track; and
   c. said lower face has a second guide track.

6. A device for taking an impression of an upper and a lower bite of a dental patient comprising:
   a. a layer of hard wax shaped for insertion into the mouth of said patient, said layer of hard wax having an upper surface and a lower surface;
   b. a first layer of soft wax attached to said layer of hard wax proximate said upper surface;
   c. a second layer of soft wax attached to said layer of hard wax proximate said lower surface;
   d. first and second ends defining a substantially horse-shoe shape with an open segment and a closed segment, and a handle attached to said device between said first end and said second end; and
   e. said layer of hard wax increases proportionally in thickness from said closed segment toward said open segment thereby adapting said device to stimulate said patient's upper and lower jaws into a position of centric occlusion.

7. A device for taking an impression of an upper and a lower bite of a dental patient comprising:
   a. a layer of hard wax shaped for insertion into the mouth of said patient, said layer of hard wax having an upper surface and a lower surface;
   b. a first layer of soft wax attached to said layer of hard wax proximate said upper surface; and
   c. a second layer of soft wax attached to said layer of hard wax proximate said lower surface; and
   d. recessed areas in said upper surface and said lower surface of said layer of hard wax, said recessed areas corresponding to ridges in said layers of soft wax.

8. A device for determining a centric occlusion of an upper and a lower of a patient each having teeth and gingiva comprising:
   a. means for holding said device;
   b. means for determining the centric occlusion of said teeth attached to said means for holding said device comprising a layer of hard wax having an upper surface and a lower surface;
   c. means for determining the centric occlusion of said gingiva attached to said means for determining the centric relation of said teeth comprising a layer of soft wax having ridges; and d. recessed areas in said upper surface and said lower surface of said layer of hard wax, said recessed areas corresponding to ridges in said layers of soft wax.

9. The device of claim 8 wherein said means for holding said device comprises a handle.

10. The device of claim 8 wherein:
   a. said device is U-shaped and has a closed segment and an open segment; and
   b. said layer of hard wax increases proportionally in thickness from said closed segment toward said open segment thereby adapting said device to stimulate said patient's upper and lower jaws into a position of centric occlusion.

11. The device of claim 10 wherein said soft wax comprises beeswax.

12. The device of claim 8 wherein:
   a. said device has a first face and a second face;
   b. said first face has a first guide track; and
   c. said second face has a second guide track.

13. The device of claim 8 wherein said device is substantially horse-shoe shaped having a first end and a second end and said handle is attached between said first end and said second end.

14. The device of claim 13 wherein said first end can be adjusted in relation to said second end.

15. A method of obtaining an impression to determine a tentative centric relation between upper and lower dental tissues of a patient comprising the steps of:
   a. softening in warm water a dental impression device comprising a layer of hard wax placed between layers of soft wax until said device is manually moldable, said device having recessed areas in said upper surface and said lower surface of said layer of hard wax, said recessed areas corresponding to ridges in said layers of soft wax;
   b. adjusting said softened device to the width of the mandibular and maxillary arches of said patient and molding said device to proximately occupy the existing interocclusal space of said patient;
   c. retracting the mandible of said patient to a posterior position; and
   d. positioning said device within said interocclusal space and directing said patient to bite down on said device from the back of said dental tissues.

* * * * *